(12) United States Patent
Herdt et al.

(10) Patent No.: US 8,617,466 B2
(45) Date of Patent: Dec. 31, 2013

(54) ELECTROLYTIC DEGRADATION SYSTEMS AND METHODS USABLE IN INDUSTRIAL APPLICATIONS

(75) Inventors: Brandon L. Herdt, Hastings, MN (US); Junzhong Li, Apple Valley, MN (US)

(73) Assignee: Ecolab USA Inc., St. Paul, MN (US)

( * ) Notice: Subject to any disclaimer, the term of this patent is extended or adjusted under 35 U.S.C. 154(b) by 428 days.

(21) Appl. No.: 12/871,660

(22) Filed: Aug. 30, 2010

(65) Prior Publication Data

US 2011/0052445 A1 Mar. 3, 2011

Related U.S. Application Data

(60) Provisional application No. 61/239,628, filed on Sep. 3, 2009.

(51) Int. Cl.
*A61L 2/00* (2006.01)
*B01D 17/06* (2006.01)

(52) U.S. Cl.
USPC ............. 422/28; 422/1; 422/22; 422/186.04; 210/748.01; 210/748.16; 210/749; 205/687

(58) Field of Classification Search
USPC ............... 422/1, 22, 28, 186.04; 210/748.01, 210/748.16, 749; 205/687; 137/237; 204/194, 242, 280
See application file for complete search history.

(56) References Cited

U.S. PATENT DOCUMENTS

| | | | |
|---|---|---|---|
| 2,833,813 A | 5/1958 | Wallace | |
| 3,825,445 A | 7/1974 | Mac Carthy | |
| 4,571,292 A | 2/1986 | Liu | |
| 4,680,163 A * | 7/1987 | Blidschun et al. | ............ 422/28 |
| 4,857,152 A | 8/1989 | Armstrong | |
| 5,306,352 A | 4/1994 | Nicolson et al. | |
| 5,364,510 A | 11/1994 | Carpio | |
| 5,368,867 A | 11/1994 | Da Silva et al. | |
| 5,395,493 A | 3/1995 | Pinkowski | |
| 5,400,818 A | 3/1995 | Cosentino | |
| 5,470,484 A | 11/1995 | Mcneel | |
| 5,503,720 A | 4/1996 | Teske | |
| 5,647,891 A | 7/1997 | Blizzard | |
| 5,882,590 A | 3/1999 | Stewart | |
| 5,972,196 A | 10/1999 | Murphy et al. | |
| 6,083,377 A * | 7/2000 | Lin et al. | ...................... 205/617 |
| 6,171,551 B1 | 1/2001 | Malchesky et al. | |
| 6,326,032 B1 | 12/2001 | Richter | |
| 6,387,238 B1 | 5/2002 | Merk et al. | |
| 6,558,529 B1 | 5/2003 | McVey | |

(Continued)

FOREIGN PATENT DOCUMENTS

| | | |
|---|---|---|
| EP | 0223479 A2 | 3/1986 |
| EP | 269435 A2 | 6/1988 |

(Continued)

OTHER PUBLICATIONS

International Search Report and Written Opinion mailed Jun. 1, 2011.

(Continued)

*Primary Examiner* — Monzer Chorbaji
(74) *Attorney, Agent, or Firm* — Merchant & Gould PC (57) ABSTRACT

The present disclosure relates to the use of a split and single electrical cells in industrial applications, and particularly in aseptic packaging applications.

6 Claims, 5 Drawing Sheets

(56) References Cited

U.S. PATENT DOCUMENTS

| | | |
|---|---|---|
| 6,712,949 B2 | 3/2004 | Gopal |
| 6,761,815 B2 | 7/2004 | Nakajima et al. |
| 6,793,903 B1 | 9/2004 | Parrish |
| 6,844,742 B2 | 1/2005 | Centanni |
| 6,949,178 B2 | 9/2005 | Tennakoon et al. |
| 7,150,884 B1 | 12/2006 | Hilgren et al. |
| 7,349,760 B2 | 3/2008 | Wei |
| 7,723,281 B1 | 5/2010 | Herdt et al. |
| 2002/0128312 A1 | 9/2002 | Hei |
| 2002/0192340 A1 | 12/2002 | Swart |
| 2003/0175983 A1 | 9/2003 | Wei |
| 2004/0043283 A1 | 3/2004 | Cipollini et al. |
| 2004/0197252 A1 | 10/2004 | Parrish |
| 2004/0220416 A1 | 11/2004 | Emsenhuber et al. |
| 2005/0095355 A1 | 5/2005 | Leistra et al. |
| 2005/0151117 A1 | 7/2005 | Man |
| 2006/0071225 A1 | 4/2006 | Beeson et al. |
| 2007/0010420 A1 | 1/2007 | Lange |
| 2007/0108056 A1* | 5/2007 | Nyberg et al. ............ 204/554 |
| 2008/0233251 A1 | 9/2008 | Sizer |
| 2008/0274242 A1 | 11/2008 | Gutzmann |
| 2009/0026932 A1 | 1/2009 | Kwak |
| 2009/0148342 A1* | 6/2009 | Bromberg et al. ............ 422/37 |
| 2009/0312292 A1 | 12/2009 | Rovison |
| 2010/0108942 A1 | 5/2010 | Man |

FOREIGN PATENT DOCUMENTS

| | | |
|---|---|---|
| EP | 411970 A1 | 2/1991 |
| EP | 833149 A1 | 4/1998 |
| EP | 1 382 666 A1 | 1/2004 |
| JP | 2007-167160 | 7/2007 |
| JP | 2009-507887 | 2/2009 |
| WO | WO9510191 A1 | 4/1995 |
| WO | WO9528635 A1 | 10/1995 |
| WO | WO00/64842 | 3/2000 |
| WO | WO00/61524 | 10/2000 |
| WO | WO2004/067448 | 8/2004 |
| WO | WO2006/071225 | 7/2006 |
| WO | WO2006/108492 | 10/2006 |
| WO | WO2007/042114 | 4/2007 |

OTHER PUBLICATIONS

Brett A. Wagner, et al., "Inactivation of anthracyclines by serum heme proteins," *Chemical Research in Toxicology* (2007), vol. 20(6), pp. 920-926.

Xuehui Li, et al., "Ultrasonic chemical oxidative degradations of 1,3-dialkylimidazolium ionic liquids and their mechanistic elucidations", *Dalton Transactions* (2007), vol. 19, pp. 1875-1880.

Giancarlo Cravotto, et al., "A new flow reactor for the treatment of polluted water with microwave and ultrasound," *Journal of Chemical Technology and Biotechnology* (2007), Vo. 82(2), pp. 205-208.

T. Suzuki, et al., "Oxidation and dissolution rates of $UO_2(s)$ in carbonate-rich solutions under external alpha irradiation and initially reducing conditions," *Radiochimica Acta* (2006), vol. 94(9-11), pp. 567-573.

J.A. Raust, et al., "Stability studies of ionised and non-ionised 3,4-diaminopyridine: Hypothesis of degradation pathways and chemical structure of degradation products," *Journal of Pharmaceutical and Biomedical Analysis* (2007), vol. 43(1), pp. 83-88.

C. Gravato, et al., "Oxidative stress, liver biotransformation and genotoxic effects induced by copper in Anguilla anguilla L.—the influence of pre-exposure to β-naphthoflavone," *Chemosphere* (2006), vol. 65(10), pp. 1821-1830.

Ming Hu, et al., "Purification and characteristics of a low-molecular-weight peptide possessing oxidative capacity for phenol from Phanerochaete chrysosporium," *Science in China, Series C: Life Sciences* (2006), vol. 49(3), pp. 243-250.

Romana Sulakova, et al., "Oxidation of azo textile soluble dyes with hydrogen peroxide in the presence of Cu(II)-chitosan heterogeneous catalysts," *Dyes and Pigments* (2006), vol. Date 2007, vol. 73(1), pp. 19-24.

Flavia C. Moura et al, "Investigation of reaction mechanisms by electrospray ionization mass spectrometry: characterization of intermediates in the degradation of phenol by a novel iron/magnetite/hydrogen peroxide heterogeneous oxidation system," *Rapid Communications in Mass Spectrometry* (2006), vol. 20(12), pp. 1859-1863.

Mi-Young Lee, et al., "Protective effects of cathodic electrolyzed water on the damages of DNA, RNA and protein," *Water Contamination Emergencies* (2006), pp. 320-323.

Samuele Meinero, et al., "Oxidative and energetic efficiency of different electrochemical oxidation processes for chloroanilines abatement in aqueous medium," *Chemosphere* (2006), vol. 64(3), pp. 386-392.

Jonathan F. Ojo, et al., "Organosulfur oxoacids. Part 1. Synthesis, structure, and reactivity of dimethylaminoiminomethanesulfinic acid (DMAIMSA)," *Canadian Journal of Chemistry* (2006), vol. 84(5), pp. 825-830.

N. Genc, et al., "Photooxidation: a decolorization procedure and a pre-treatment step for biodegradation of reactive azo dye," *Polish Journal of Environmental Studies* (2006), vol. 15(1), pp. 73-79.

V.P. Shilov, et al., "Catalytic decomposition of organic anions in alkaline radioactive waste: III. Oxidation of oxalate and glycolate," *Radiochemistry* (2006), vol. 48(1), pp. 36-40.

S. Sandhya, et al., "Degradation and decolorization of tannery dye acid blue 113 by photo, Fenton's and microbial oxidation," *Journal of Indian Association for Environmental Management* (2005), vol. 32(3), pp. 155-160.

David H. Bremner, et al., "Phenol degradation using hydroxyl radicals generated from zero-valent iron and hydrogen peroxide," *Applied Catalysis, B: Environmental* (2006), vol. 63(102), pp. 15-19.

Manfred Lehnig, et al., "15N CIDNP investigations of the peroxynitric acid nitration of L-tyrosine and of related compounds," *Organic and Biomolecular Chemistry* (2006), vol. 4(4), pp. 721-729.

Mohammad H. Entezari, et al., "A combination of ultrasound and a bio-catalyst: removal of 2-chlorophenol from aqueous solution," *Ultrasonics Sonochemistry* (2006), vol. 13(1), pp. 37-41.

Fatma Guel Boyaci, et al., "Nucleophile influence on the complex reaction network of 2-isopropylnaphthalene hydroperoxide decomposition," *Chemical Engineering and Processing* (2005), vol. 44(11), pp. 1197-1206.

V. Christian, et al., "Degradation of xenobiotic compounds by lignin-degrading white-rot fungi: Enzymology and mechanisms involved," *Indian Journal of Experimental Biology* (2005), vol. 43(4), pp. 301-312.

Martin Krusa, et al., "Oxidative cellulose degradation by cellobiose dehydrogenase from Phanerochaete chrysosporium: A model compound study," *Holzforschung* (2005), vol. 59(3), pp. 263-268.

Samuel D. Fisher, et al., "Effects of potassium permanganate and hydrogen peroxide on the biodegradation of weathered crude oil in sediments from Indiana Harbor Canal," *WEFTEC.04, Conference Proceedings, Annual Technical Exhibition & Conference* (2004), pp. 627-632.

Yuriy N. Kozlov, et al., "Oxidations by the reagent "$O_2$-$H_2O_2$-vanadium derivative-pyrazine-2- carboxylic acid"," *Journal of Molecular Catalysis A: Chemical* (2005), vol. 227(1-2), pp. 247-253.

Zhaoqi Zhang, et al., "Role of peroxidase in anthocyanin degradation in litchi fruit pericarp," *Food Chemistry* (2004), vol. 90(1-2), pp. 47-52.

James Thomson, et al., "Vacuum ultraviolet irradiation for natural organic matter removal," *Journal of Water Supply: Research and Technology—AQUA* (2004), vol. 53(4), pp. 193-206.

Georgiy B. Shul'pin, et al., "Hydrogen peroxide oxygenation of alkanes including methane and ethane catalyzed by iron complexes in acetonitrile," *Advanced Synthesis & Catalysis* (2004), vol. 346(2+3), pp. 317-332.

J.S. Goldik, et al., "Surface electrochemistry of UO2 in dilute alkaline hydrogen peroxide solutions," *Electrochimica Acta* (2004), vol. 49(11), pp. 1699-1709.

Mirat D. Gurol, "Improvement of biodegradability of persistent organic compounds by chemical oxidation," *Annual Industrial Wastes Technical and Regulatory Conference* (2002), pp. 516-526.

Annele Hatakka, et al., "Manganese peroxidase and its role in the degradation of wood lignin," *ACS Symposium Series* (2003), 855 (Applications of Enzymes to Lignocellulosics, pp. 230-243.

(56) References Cited

OTHER PUBLICATIONS

T. McCue, et al., "Degradation of halogenated aliphatic compounds utilizing sequential anaerobic/aerobic treatments," *Water Science and Technology* (2003), vol. 47(10), pp. 79-84.

Lan-Ian Wang, "Effect of the composition of oxygen electrode on catalytic activity," *Anhui Gongcheng Keji Xueyuan Xuebao, Ziran Kexueban* (2003), vol. 18(2), pp. 12-14.

G. Amitai, et al., "Degradation of VX and sulfur mustard by enzymatic haloperoxidation," *Journal of Applied Toxicology* (2003), vol. 23(4), pp. 225-233.

J. Aaron Frim, et al., Sonochemical destruction of free and metal-binding ethylenediaminetetraacetic acid, *Water Research* (2003), vol. 37(13), pp. 3155-3163.

Norimichi Takenaka, et al., "Rapid reaction of sulfide with hydrogen peroxide and formation of different final products by freezing compared to those in solution," *International Journal of Chemical Kinetics* (2003), vol. 35(5), pp. 198-205.

Wei Wang, et al., "A peptide-mediated and hydroxyl radical HO.-involved oxidative degradation of cellulose by brown-rot fungi," *Biodegradation* (2003), vol. Date 2002, 13(6), pp. 383-394.

Zewen Liao, et al., "Characterization of nC7-soluble fractions of the products from mild oxidation of asphaltenes," *Organic Geochemistry* (2002) vol. 33(12), pp. 1477-1486.

Dietmar Schlosser, et al.., Laccase-catalyzed oxidation of Mn2+ in the presence of natural Mn3+chelators as a novel source of extracellular $H_2O_2$ production and its impact on manganese peroxidase, *Applied and Environmental Microbiology* (2002), vol. 68(7), pp. 3514-3521.

Susan W. Havorka, et al., "Oxidative degradation of a sulfonamide-containing 5,6-dihydro-4-hydroxy-2- pyrone in aqueous/organic cosolvent mixtures," *Pharmaceutical Research* (2002), vol. 19(4), pp. 538-545.

Wataru Kamimura, et al., "Transience in polyion complexation between nicotinamide-modified dextran and carboxymethyl dextran during enzymatic degradation of dextran," *Journal of Biomaterials Science, Polymer Edition* (2001), vol. 12(10), pp. 1109-1122.

C. Vinas, et al., "Proton Mediated Partial Degradation of Closo-dicarbaboranes," *Inorganic Chemistry* (2001), vol. 40(14), pp. 3259-3260.

Wataru Kamimura, et al., "Self-complex formation of nicotinamide-modified dextran with carboxymethyl dextran using their degradation products," *Journal of Biomaterials Science, Polymer Edition* (2000), vol. 11(7), pp. 747-765.

Shelley A. Allen, et al., "Remediation of contaminated soils by combined chemical and biological treatments," *Physical and Thermal Technologies: Remediation of Chlorinated and Recalcitrant Compounds, International Conference on Remediation of Chlorinated and Recalcitrant Compounds* (2000), pp. 301-306.

S.B. Eskander, et al., "Wet oxidative degradation of cellulosic wastes. 3: Decomposition of tissue paper," *International Conference Proceedings on Radioactive Waste Management and Environmental Remediation* (1999), pp. 1336-1342.

Facundo J. Marquez-Rocha, et al., "Biodegradation of soil-adsorbed polycyclic aromatic hydrocarbons by the white rot fungus Pleurotus ostreatus," *Biotechnology Letters* (2000), vol. 22(6), pp. 469-472.

C.D. Adams, et al., "Effects of UV/$H_2O_2$ preoxidation on the aerobic biodegradability of quaternary amine surfactants," *Water Research* (1999), vol. 34(2), pp. 668-672.

G. Centi, et al., "Catalytic wet oxidation with $H_2O_2$ of carboxylic acids on homogeneous and heterogeneous Fenton-type catalysts," *Catalysis Today* (2000), vol. 55(1-2), pp. 61-69.

Fatma Guel Boyaci, et al., "Decomposition of 2-isopropylnaphthalene hydroperoxide into 2-naphthol and acetone in the presence of acetic acid and $H_2O_2$," *Industrial & Engineering Chemistry Research* (1999), vol. 38(10), pp. 3838-3846.

A.I. Kokorin, "Oxidative processes in polymer—metal complexes. A new way to prepare polyampholytes with groups of α-picolinic acid," *Oxidation Communications* (1999), vol. 22(1), pp. 68-74.

Shinichi Kinoshita, et al., "Bacterial lignin degradation and hydroquinone peroxidase," *Biotechnology for Sustainable Utilization of Biological Resources in the Tropics* (1997), vol. 11, pp. 58-70.

G. Carotenuto, et al., "XPS study of the polyethylene degradation in the body environment," *Polymer News* (1998), vol. 23(10), pp. 352-354.

G.L. Picciolo, et al., "Effect of oxidizing environments on pyrolytic carbon," *Cells and Materials* (1996), vol. 6 (4), pp. 291-302.

F. Todo, et al., "Decomposition of organic wastes by wet-oxidation with hydrogen peroxide oxidant," *Proceedings of the International Conference on Radioactive Waste Management and Environmental Remediation* (1995), vol. 2, pp. 1099-1101.

Jimmy Kao, et al., "Remediation of dioxin contaminated soil enhanced by chemical oxidation pretreatment," *Contaminated Soils* (1997), vol. 2, pp. 191-203.

J.M. Aubry, et al., "Generation of singlet oxygen from the catalytic system $H_2O_2$/Ca(OH)$_2$ and applications to the selective oxidation of unsaturated compounds," *Studies in Surface Science and Catalysis* (1997), vol. 110, pp. 883-892.

C. -J Lu, et al., "The utilization efficiency of hydrogen peroxide on the removal of volatile organic acids in sand columns," *Water Science and Technology* (1996), vol. 34(7-8, Water Quality International '96, Part 4), pp. 359-364.

Miriam H.A. Van Eekert, et al., "Removal of tetrachloromethane by granular methanogenic sludge," *Bioremediation of Chlorinated Solvents, [Papers from the International in Situ and On-Site Bioreclamation Symposium]* (1995), pp. 139-145.

Yoshitaka Mirishita, et al., "Degradation of ascorbic acid by Cu2+,"*Seibutsu Shiryo Bunseki* (1994), vol. 17(3), pp. 205-212.

B.S. Girgis, et al., "Catalytic decomposition of $H_2O_2$ over magnesium hydroxide impregnated with manganous ions," *Bulletin of the National Research Centre (Egypt)* (1993), vol. 18(2), pp. 85-93.

Henryk Matusiewicz, et al., "Comparison of the efficiencies of online and high-pressure closed vessel approaches to microwave heated sample decomposition," *Fresenius' Journal of Analytical Chemistry* (1994), vol. 349(6), pp. 428-433.

Otilia Costisor, et al., "Hydrogen peroxide decomposition in the presence of some Cu(II)-Co(II) complex compounds," *Chemical Bulletin of the Technical University of Timisoara* (1992), vol. 37(51), pp. 31-39.

Velichka Dimitrova, et al., "Hydrogen peroxide decomposition on the surface of Ni and Ni75B25 amorphous alloy," *Godishnik na Sofiiskiya Universitet Sv. Kliment Okhridski, Khimicheski Fakuhet* (1993), vol. 86, pp. 137-144.

K. Halden, "Methanotrophic bacteria for the in-situ renovation of polluted aquifers," *Process Safety and Environmental Protection* (1991), vol. 69(B3), pp. 173-179.

"Surfactant Encyclopedia," Cosmetics and Toiletries, vol. 104, (2), pp. 86-96 (1989).

"Electrolytic Synthesis if Peroxyacetic Acid Using In Situ Generated Hydrogen Peroxide on Gas Diffusion Electrodes," *Journal of The Electrochemical Society*, pp. D93-D97 (Aug. 18, 2004).

Kirk-Othmer, "Encyclopedia of Chemical Technology," Third Edition, vol. 8, ©1979 by John Wiley & Sons, Inc., pp. 900-912.

\* cited by examiner

ELECTROLYTIC DEGRADATION SYSTEMS AND METHODS USABLE IN INDUSTRIAL APPLICATIONS

FIELD

The present disclosure relates to use of electrical cells usable in industrial applications, and particularly in aseptic packaging applications.

BACKGROUND

In the food, beverage and dairy markets, a wide array of shelf stable packaged liquid and semi-liquid foods exist. Shelf stable foods are food products that have been processed so they can be safely stored and sold under non-refrigerated conditions in a sealed container while having a useful shelf life. These foods range from canned soups to highly acidified soda and sport drinks. Various techniques are used to produce shelf stable foods. One such technique is aseptic packaging. In a typical aseptic packaging procedure, a liquid food product is thermally sterilized while the food product packaging is separately chemically sterilized. The sterile food product and sterile packaging are then brought together and sealed under sterile conditions. This results in a shelf stable food product.

Chemical sterilization of the food product packaging is often performed in an aseptic packaging filler. Aseptic packaging fillers use a chemical sterilant to sterilize the food product packaging. Common aseptic fillers include a single-use filler and a re-use or recirculating filler. A single use filler uses a stock solution of sterilant. The filler deposits the sterilant on the inside and sometimes outside of packaging to sterilize it. The sterilant can be heated at the point of depositing or it can be pre-heated prior to depositing onto the packaging. Also, certain running conditions (e.g., temperature, contact time and concentration) are chosen so that the packaging is rendered commercially sterile. After being deposited inside of the packaging, the spent sterilant drains from the packaging and is exported by the filler either to a drain or to other parts of the machine for different treatments (such as treating an exterior of the packaging). In a single-use filler, once the sterilant is used, it is discarded.

A re-use or re-circulating filler contains a sump of sterilant. This sump is held at a desired temperature so that the sterilant is also maintained at a desired temperature. The filler draws sterilant from this sump and uses it to sterilize inside and/or outside of the food packaging. The sterilant then drains away from the packaging and it is collected and exported back to the same sump which it originated.

After the packaging is treated by either type of filler, it is rinsed with microbiologically pure water, filled with a food product and sealed. All of these steps occur under sterile conditions inside of the filler.

One commonly used chemical sterilant is a peracid solution. In this solution, peracid exists in equilibrium with its corresponding carboxylic acid and hydrogen peroxide. The equilibrium shifts to the reactant side or the product side of the chemical equilibrium equation based on the concentration of reactants or products present in a given solution.

Normally, a peracid solution is provided to an end-user as an equilibrium concentrate and the end-user dilutes the concentrate to the level that is required for microbial treatment of their surface of interest. When peracid solutions are used in a re-circulating filler, they are re-circulated back to a sump for extended periods of time. Over time, the peracid inside the sump slowly degrades or equilibrates back to the carboxylic acid and hydrogen peroxide. As a result, the sump accumulates higher levels of hydrogen peroxide and carboxylic acid. Filler operators have specifications set for maximum levels of hydrogen peroxide or carboxylic acid in the sump. When the sump approaches these maximum levels, the filler must be shut down, drained and refilled with fresh solution. Other filler operators set up fillers so that they have a certain bleed off rate. Adjusting the bleed off rate modifies the accumulation rate of peroxide and carboxylic acid in the sump so that the filler can be run for an extended length of time.

Additionally, other operators include catalase enzymes in the peracid solution, in order to reduce hydrogen peroxide in the solution. In such cases, operators must strictly monitor the hydrogen peroxide concentration and periodically add the enzymes into the solution when hydrogen peroxide reaches certain levels. The solution must also be provided at specific temperatures and within certain pH ranges in order for these enzymes to work.

Further, once the package is rinsed, e.g. with pure water, the rinse undesirably accumulates residues from the sterilant and is removed from the system.

All of these procedures unnecessarily increase the amount of water, energy, chemistry and complexity required to operate an aseptic filler. It is against this background that the present disclosure has been made.

DEFINITIONS

For the following defined terms, these definitions shall be applied, unless a different definition is given in the claims or elsewhere in this specification.

As used herein, the term "split cell" or "electrical split cell" means an electrolytic cell where an anode and a cathode are separated from one another by a salt bridge that allows the flow of current between the anode and cathode but retards wholesale transfer of the bulk liquid from one side of the cell to the other. Any known salt bridge or semi-permeable membrane in the art can be used, including ion selective membranes, high density fiber meshes, and gels.

As used herein, the term "single cell" or "electrical single cell" means an electrolytic cell where an anode and a cathode are included in the cell.

The term "anode" refers to any positively charged electrode and the term "cathode" refers to any negatively charged electrode.

All numeric values are herein assumed to be modified by the term "about," whether or not explicitly indicated. The term "about" generally refers to a range of numbers that one of skill in the art would consider equivalent to the recited value (i.e., having the same function or result). In many instances, the term "about" may include numbers that are rounded to the nearest significant figure.

Weight percent, percent by weight, % by weight, wt %, and the like are synonyms that refer to the concentration of a substance as the weight of that substance divided by the weight of the composition and multiplied by 100.

The recitation of numerical ranges by endpoints includes all numbers subsumed within that range (e.g. 1 to 5 includes 1, 1.5, 2, 2.75, 3, 3.80, 4 and 5).

As used in this specification and the appended claims, the singular forms "a," "an," and "the" include plural referents unless the content clearly dictates otherwise. Thus, for example, reference to a composition containing "a compound" includes a mixture of two or more compounds. As used in this specification and the appended claims, the term "or" is generally employed in its sense including "and/or" unless the content clearly dictates otherwise.

The use of the terms "antimicrobial" in this application does not mean that any resulting products are approved for use as an antimicrobial agent.

SUMMARY

First, surprisingly, it has been discovered that use of electricity in a split cell is particularly effective at selectively degrading hydrogen peroxide in peracid compositions. It has also been discovered that such an electrolytic degradation process is particularly advantageous when used in industrial operations, such as aseptic filling operations.

The use of the electricity in a split cell to selectively degrade hydrogen peroxide in aseptic filling operations is beneficial because peroxide builds in concentration over time as a peracid solution is re-circulated in a filler. This creates two problems. First, at some point the peroxide accumulates to a point that it can no longer be effectively rinsed from the treated bottles or removed via filtration of rinse water. To overcome these issues, all or a portion of the peracid solution must be diluted with fresh water and fresh peracid chemistry creating waste of both water and chemistry. Secondly, an optimization of microbial efficacy can be maintained by keeping a ratio of peracid:hydrogen peroxide below 5:1. In a re-circulated system this can not be maintained without some means of selectively degrading hydrogen peroxide. The addition of catalase to the solution has been identified as a potential path to remediate the build-up of peroxide over time but it suffers from limited stability that requires that its dosage be closely monitored and controlled. An electrolytic method of eliminating hydrogen peroxide is beneficial because it is stable, requires no dosing control, and does not require addition of a second chemistry to mitigate the negative effects of hydrogen peroxide as outlined above.

Accordingly, this disclosure relates to a method of selectively degrading hydrogen peroxide in an antimicrobial composition, comprising providing an antimicrobial composition comprising hydrogen peroxide, carboxylic acid, and peracid, providing a split cell in fluid communication with the antimicrobial composition in order to degrade the hydrogen peroxide while not degrading the carboxylic acid and the peracid. In some cases, the split cell is used to degrade at least 500 pm of the hydrogen peroxide in less than 15 minutes. In other cases, the split cell is used to maintain predetermined amounts of the hydrogen peroxide, the carboxylic acid, and the peracid. The predetermined amounts of the hydrogen peroxide, the carboxylic acid, and the peracid can be:

from about 0.00001% to about 0.5 wt. % hydrogen peroxide;

from about 0.1% to about 20.0 wt. % of a $C_1$-$C_{10}$ carboxylic acid; and from about 0.1% to about 2.0 wt. % of a $C_1$-$C_{10}$ peracid.

In certain embodiments, the split cell comprises a first loop and a second loop that are in electrical communication with one another using a salt bridge and a power supply that transmits an electric potential between the first loop and the second loop, wherein the first loop contains a cathode and the second loop contains an anode and the first loop contains an antimicrobial composition and the second loop contains a reducing solution, the reducing solution being capable of accepting electrons from the antimicrobial composition and capable of transmitting electrical current through the salt bridge into the first loop. The method can further include monitoring the amounts of the hydrogen peroxide, the carboxylic acid and/or the peracid and adjusting the electric potential in order to maintain predetermined amounts of the hydrogen peroxide, the carboxylic acid, and the peracid. In many cases, the method is part of an aseptic packaging method.

A system for maintaining predetermined amounts of hydrogen peroxide, carboxylic acid, and peracid in an antimicrobial composition is also provided, which includes a split cell comprising a first loop and a second loop that are in electrical communication with one another using a salt bridge and a power supply that transmits an electric potential between the first loop and the second loop, wherein the first loop contains a cathode and the second loop contains an anode and the first loop contains an antimicrobial composition, the antimicrobial solution containing predetermined amounts of hydrogen peroxide, carboxylic acid and peracid, and wherein the second loop contains a reducing solution, the reducing solution being capable of accepting electrons from the antimicrobial composition and capable of transmitting electrical current through the salt bridge into the first loop. The predetermined amounts of hydrogen peroxide, carboxylic acid, and peracid can be:

from about 0.00001% to about 0.5 wt. % hydrogen peroxide;

from about 0.1% to about 20.0 wt. % of a $C_1$-$C_{10}$ carboxylic acid; and from about 0.1% to about 2.0 wt. % of a $C_1$-$C_{10}$ peracid.

Further, in some cases, the carboxylic acid is selected from the group consisting of acetic acid, octanoic acid, and mixtures thereof, and the peracid is selected from the group consisting of peracetic acid, peroctanoic acid, and mixtures thereof. The system can further include a regulator that measures amounts of hydrogen peroxide and/or peracid and adjusts the electric potential in order to maintain the predetermined amounts of hydrogen peroxide, carboxylic acid, and peracid.

A method of disinfecting packages through aseptic packaging is also provided, which includes providing an antimicrobial composition having desired components, applying the antimicrobial composition to a surface of a food package in an amount sufficient to render a final food product located in the food package suitable for distribution and sale under non-refrigerated storage conditions, providing a split cell in fluid communication with the antimicrobial composition, and using the split cell to maintain predetermined amounts of the desired components in the antimicrobial composition. In certain cases, the desired components are hydrogen peroxide, carboxylic acid, and peracid. The predetermined amounts of hydrogen peroxide, carboxylic acid, and peracid can be:

from about 0.00001% to about 0.5 wt. % hydrogen peroxide;

from about 0.1% to about 20.0 wt. % of a $C_1$-$C_{10}$ carboxylic acid; and from about 0.1% to about 2.0 wt. % of a $C_1$-$C_{10}$ peracid.

Also, the carboxylic acid can be selected from the group consisting of acetic acid, octanoic acid, and mixtures thereof, and the peracid can be selected from the group consisting of peracetic acid, peroctanoic acid, and mixtures thereof.

An aseptic packaging system is also provided, which includes a sump, a sterilizing area, a first line that transfers an antimicrobial composition from the sump to the sterilizing area wherein the antimicrobial composition comprises predetermined amounts of desired components, a second line that transfers the antimicrobial composition from the sterilizing area back to the sump or to a drain, one or more optional heaters integrated into the second line and/or the first line, and a split cell integrated into the sump, the first line, the second line, or the one or more optional heaters, wherein the split cell maintains the predetermined amounts of desired components in the antimicrobial composition. The desired components can be hydrogen peroxide, carboxylic acid, and peracid. Also, the predetermined amounts of hydrogen peroxide, carboxylic acid, and peracid can be:

from about 0.00001% to about 0.5 wt. % hydrogen peroxide;

from about 0.1% to about 20.0 wt. % of a $C_1$-$C_{10}$ carboxylic acid; and from about 0.1% to about 2.0 wt. % of a $C_1$-$C_{10}$ peracid.

Also, the carboxylic acid can be selected from the group consisting of acetic acid, octanoic acid, and mixtures thereof, and the peracid can be selected from the group consisting of peracetic acid, peroctanoic acid, and mixtures thereof.

The split cell of the aseptic packaging system can include a first loop and a second loop that are in electrical communication with one another using a salt bridge, wherein the first loop contains a cathode and the second loop contains an anode, and a power supply that transmits an electric potential between the first loop and the second loop, wherein the first loop contains an antimicrobial composition and the second loop contains a reducing solution, the reducing solution being capable of accepting electrons from the antimicrobial composition and capable of transmitting electrical current through the salt bridge into the first loop. The aseptic packaging system can further include a regulator that measures amounts of hydrogen peroxide and/or peracid and adjusts the electric potential in order to maintain the predetermined amounts of hydrogen peroxide, carboxylic acid, and peracid.

A method of disinfecting packages through aseptic packaging is also provided, which includes forming an antimicrobial composition in a sump, the antimicrobial composition comprising hydrogen peroxide, carboxylic acid, and peracid, transporting the antimicrobial composition from the sump to the package using an aseptic line, applying the composition to a surface of a food package in an amount sufficient to render a final food product located in the food package suitable for distribution and sale under non-refrigerated storage conditions, integrating a split cell into the aseptic line, and using the split cell to maintain predetermined amounts of hydrogen peroxide, carboxylic acid, and peracid in the antimicrobial composition. The method can further include activating the split cell in response to a reading from a sensor that senses the amounts of hydrogen peroxide, carboxylic acid, and/or peracid or activating the split cell in a time-based manner.

Secondly, it has been discovered that the use of electricity in a single cell is effective at degrading desired components in a solution used in industrial applications, such as aseptic filling operations. For example, a single cell can be used to degrade hydrogen peroxide and peracid in certain solutions. In one embodiment, a method of non-selectively degrading hydrogen peroxide and peracid in a solution is provided, which includes the steps of providing a solution comprising hydrogen peroxide and peracid and providing a single electrolytic cell in fluid communication with the solution in order to degrade predetermined amounts of the hydrogen peroxide and the peracid. The solution can be an industrial solution such as a rinse from aseptic packaging applications or an industrial waste solution.

In another embodiment, a method of disinfecting packages through aseptic packaging is provided, including the steps of providing an antimicrobial composition having desired components, applying the antimicrobial composition to a surface of a food package in an amount sufficient to render a final food product located in the food package suitable for distribution and sale under non-refrigerated storage conditions, applying a rinse to the surface of the food package after applying the antimicrobial composition; and using a single cell to degrade predetermined amounts of desired components in the used rinse. In some cases, the antimicrobial composition comprises hydrogen peroxide, carboxylic acid, and peracid and the desired components in the used rinse include hydrogen peroxide and peracid.

Other embodiments provide for an aseptic packaging system, which includes a sterilizing area, a first line that transfers an antimicrobial composition to a sterilizing area, wherein the antimicrobial composition comprises predetermined amounts of desired components, a second line that transfers the antimicrobial composition away from the sterilizing area, a third line that transfers a rinse to the sterilizing area, a fourth line that transfers used rinse away from the sterilizing area; and a single cell integrated into the third line or fourth line, wherein the single cell degrades predetermined amounts of desired components in the used rinse. In some cases, the desired components of the antimicrobial composition are hydrogen peroxide, carboxylic acid, and peracid and the desired components of the used rinse are hydrogen peroxide and peracid.

These and other embodiments will be apparent to those of skill in the art and others in view of the following detailed description of some embodiments. It should be understood, however, that this summary, and the detailed description illustrate only some examples of various embodiments, and are not intended to be limiting to the invention as claimed.

DETAILED DESCRIPTION OF SOME EMBODIMENTS

The present disclosure uses a split cell to selectively degrade desired components in an antimicrobial composition. In certain embodiments, the split cell degrades hydrogen peroxide in a composition including peracid, carboxylic acid, and hydrogen peroxide. Electricity in a split cell oxidizes hydrogen peroxide to water and oxygen. The use of electricity is desirable because it is easily applied, can be controlled and does not require introduction of a secondary chemistry into a re-circulating composition. Inclusion of a second chemical in this process undesirably requires secondary dosage control, handling, monitoring and additional regulatory clearances for potential residues of the second chemistry.

In certain embodiments, a method is provided that includes the steps of: providing an antimicrobial composition and using an electrical split cell to reduce the concentration of desired components in the composition. The split cell is in fluid communication with the antimicrobial composition in a way that allows the cell to interact with and decompose the desired components.

Figure 1:
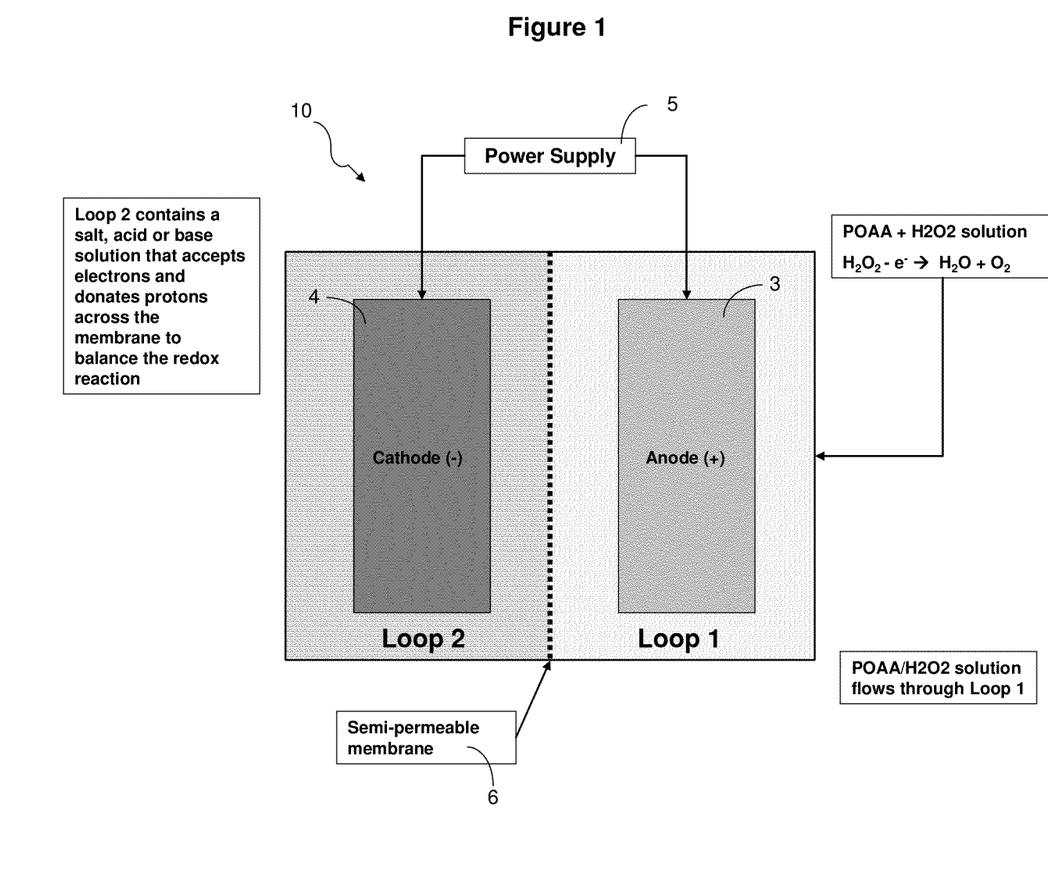
FIG. 1 shows a schematic of an exemplary split cell.

FIG. 1 illustrates an exemplary split cell. The split cell 10 includes a first loop 1 containing an anode 3 and a second loop 2 containing a cathode 4. The first loop 1 and the second loop 2 are in electrical communication via a salt bridge 6. A power supply 5 is connected to each the anode 3 and cathode 4 and transmits an electrical potential between the first loop 1 and the second loop 2. The first loop 1 contains an antimicrobial composition having predetermined amounts of certain desired components. The second loop 2 contains a reduction solution that accepts electrons and donates protons to the antimicrobial composition across the salt bridge 6. This solution can be a salt, acid, or base in some embodiments. In certain cases, the solution contains an alkaline earth salt of a carboxylic acid in the peracid solution (e.g., sodium or potassium acetate or octanoate).

The split cell can be used in any industrial application where it is desirable to selectively degrade certain desired components. Such applications include healthcare, food and beverage, warewashing, laundry, waste water treatment and housekeeping applications. For example, in the healthcare field, the split cell may be used to selectively degrade components used to sterilize medical instruments and equipment like surgical instruments and endoscopes. In the food and beverage field, the split cell may be used to selectively degrade components used to sterilize equipment, for example, clean-in-place equipment such as that found in a dairy, or shipping tanks. In warewashing and laundry applications, the split cell may be used to selectively degrade components used during a cycle of use such as a warewashing detergent, sanitizer, or rinse aid, or laundry detergent, sanitizer, bleach, or softener. In the wastewater treatment area, the split cell may be used to selectively degrade components used to treat wastewater or may be used to selectively degrade the wastewater itself as part of a method of treatment.

In some embodiments, the split cell is used to selectively degrade hydrogen peroxide in an antimicrobial composition. The antimicrobial composition can include hydrogen peroxide, carboxylic acid, and peracid. Any known carboxylic acid and peracid can be used and are discussed in further detail below. In some cases, the carboxylic acid is selected from the group consisting of acetic acid, octanoic acid, and mixtures thereof, and the peracid is selected from the group consisting of peracetic acid, peroctanoic acid, and mixtures there.

The split cell is provided in fluid communication with the antimicrobial composition in order to degrade the hydrogen peroxide while not degrading the carboxylic acid and the peracid. The split cell can be adjusted to degrade the hydrogen peroxide at any desired rate, for example to degrade 500 ppm of hydrogen peroxide in less than 15 minutes. The split cell can also be used to maintained predetermined amounts of the hydrogen peroxide, the carboxylic acid, and the peracid. In some cases, the predetermined amounts are:

from about 0.00001% to about 0.5 wt. % hydrogen peroxide;

from about 0.1% to about 20.0 wt. % of a $C_1$-$C_{10}$ carboxylic acid; and from about 0.1% to about 2.0 wt. % of a $C_1$-$C_{10}$ peracid.

In some cases, a regulator is provided that monitors and regulates the amounts of hydrogen peroxide, carboxylic acid, and peracid in order to maintain these predetermined amounts. The regulator can perform regulation functions in any desired way. In some cases, the regulator adjusts the electric potential in response to obtaining a certain measurement of the amount of hydrogen peroxide, carboxylic acid, and peracid. In other cases, the regulator adjusts the electric potential in a time-based manner.

In certain embodiments, the split cell is used in an aseptic packaging operation. Accordingly, a method of disinfecting packages using aseptic packaging is provided that includes providing an antimicrobial composition having desired components, applying the antimicrobial composition to a surface of the package in an amount that renders the final food product located in the food package suitable for distribution and sale under non-refrigerated storage conditions, providing a split cell in fluid communication with the antimicrobial composition, and using the split cell to maintain predetermined amounts of the desired components in the antimicrobial composition. Again, the desired components can be hydrogen peroxide, carboxylic acid, and peracid, as discussed above.

Figure 2:
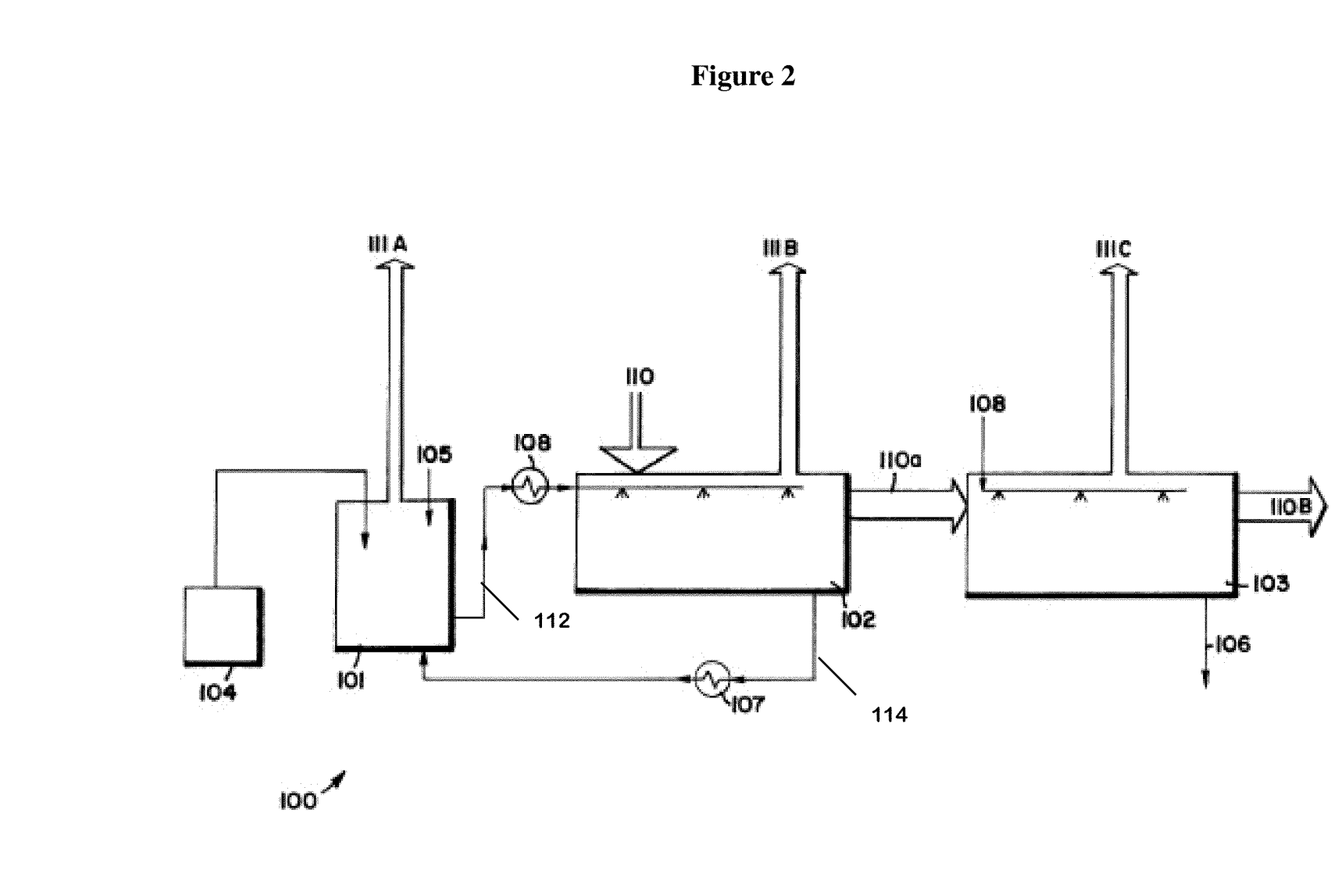
FIG. 2 shows a schematic of an exemplary bottling operation.

In certain cases, an aseptic packaging system is provided. FIG. 2 shows a schematic for an embodiment of an aseptic packaging system. FIG. 2 shows a plant 100 that can contact any desired container with an antimicrobial composition for a sanitizing regime. In FIG. 2, containers 110 are passed through a sterilizing tunnel 102. The sanitized containers 110*a* then pass through a rinsing tunnel 103 and emerge as sanitized rinsed containers 110*b*.

Examples of containers that can be treated include polyethylene terephthalate (PET), high density polyethylene (HDPE), polypropylene (PP), low density polyethylene, polycarbonate (PC), poly vinyl alcohol (PVA), aluminum, single or multilayer films or pouches, paperboard, steel, glass, multilayer bottles, other polymeric packaging material, combinations of these materials in films, pouches, bottles, or other food packaging materials.

In the process, the antimicrobial composition is added to a holding tank or sump 101. The composition can be maintained at a desired temperature in the sump 101. The composition can be transported via an aseptic line 112 and passed through a heater 108 to reach a desired temperature. The heated composition is then pumped to the sterilizing tunnel 102 and sprayed into and onto all surfaces of the containers 110. The composition can be pumped from sump 101 to the container surfaces at a desired rate.

The contact between the containers and the antimicrobial composition can be at a temperature of greater than about 0° C., greater than 25° C., or greater than about 40° C. Temperatures between about 40° C. and 90° C. can be used. In certain embodiments, contact at 40° C. to 60° C. for at least 5 sec, or at least about 10 sec, is employed.

The sanitized containers 110*a* are then drained of excess composition and then passed to a fresh water rinse tunnel 103. Fresh water 108 is provided from a fresh water make-up into the tunnel 103. The fresh water can also include a rinse additive. Within the tunnel 103, sanitized containers 110*a* are thoroughly rinsed with fresh water. The rinsed and sanitized containers 110*b* are then removed from the rinsing tunnel. Excess water drains from the tunnel via drain 106.

The sump 101, sterilizing tunnel 102 and rinsing tunnel 103 are all respectively vented to a wet scrubber or vent 111*a*, 111*b* or 111*c* to remove vapor or fumes from the system components. The antimicrobial composition that has been sprayed and drained from the containers 110*a* accumulate in the bottom of the spray tunnel 102 and is then (a) recycled through recycle line 114 and heater 107 into the sump 101, (b) moved out of the system to the drain, or (c) exported to another part of the plant.

Figure 3:
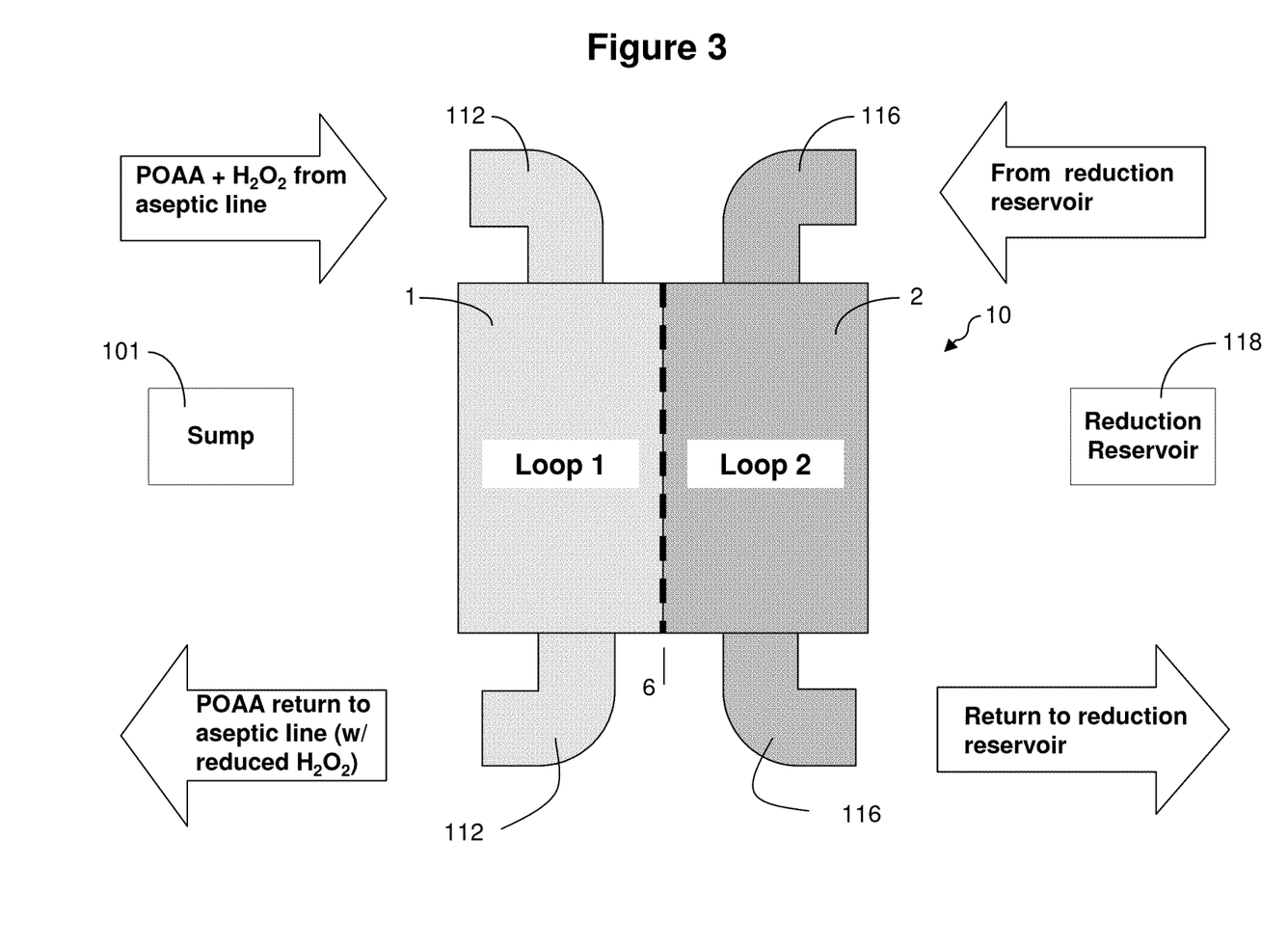
FIG. 3 shows a schematic of one embodiment of integrating a split cell into an aseptic packaging operation.

FIG. 3 illustrates a split cell 10 that is integrated with the plant 100 of FIG. 2. In FIG. 3, the split cell 10 is integrated with the aseptic line 112 of the plant 100. However, skilled artisans will understand that the cell 10 can instead be integrated with other parts of the plant 100, such as with the recycle line 114, the heaters 107, 108, or the sump 101. Likewise, the plant 100 can be of any desired design need not include only one split cell 10 and any number of split cells can be integrated with various parts of plant 100.

In the integrated split cell 10 in FIG. 3, the first loop 1 is in fluid communication with the aseptic line 112. Antimicrobial composition in the aseptic line 112 moves through loop 1. As the composition moves through loop 1, it loses electrons through application of current by the power supply (not shown). The current transfers these electrons to loop 2 of the cell where they reduce the salt/acid solution residing on the other side of the salt bridge 6. As this happens, certain desired components are degraded from the composition, so that predetermined amounts of other desired components are maintained and returned to the aseptic line 112.

At the same time, a reducing solution is present in a reservoir 118 and moves through the second loop 2 via a line 116. As the reducing solution moves through loop 2, it accepts electrons. The flow of current between loop 1 and loop 2 is facilitated by the membrane/salt bridge interface between loop 1 and 2. The reducing solution then returns to the reservoir 118 or is otherwise drained from the system. In some embodiments, the reducing solution is a single-use solution that does not recirculate. In other embodiments, the reducing solution is a recirculating solution. Replacement/replenishment of the reducing solution may be controlled automatically through inclusion of an overflow/bleed-off device whereby a portion of the reducing solution is continuously replenished with a fresh solution. It can be manually or automatically changed based on a timing mechanism linked to a dump and fill mechanism or it can be controlled externally by a pH, conductivity, or other suitable sensor.

A variety of peracid antimicrobial compositions can be used in the present methods. In certain cases, the composition includes hydrogen peroxide, carboxylic acid and peracid. Each of these components will be discussed in detail below.

Hydrogen Peroxide

The antimicrobial composition includes hydrogen peroxide. Hydrogen peroxide, $H_2O_2$, provides the advantages of having a high ratio of active oxygen because of its low molecular weight (34.014 g/mole) and being compatible with numerous substances that can be treated by the present methods because it is a weakly acidic, clear, and colorless liquid.

Another advantage of hydrogen peroxide is that it decomposes into water and oxygen. These decomposition products are advantageous because they are generally compatible with substances being treated. For example, the decomposition products are generally compatible with metallic substances (e.g., substantially noncorrosive) and with food products (e.g., does not substantially alter the color, flavor, or nutritional value of a food product). And the decomposition products are generally innocuous to incidental contact with humans and are environmentally friendly.

The composition preferably includes hydrogen peroxide in an amount effective for maintaining the equilibrium between a carboxylic acid, hydrogen peroxide, and a peracid. The amount of hydrogen peroxide should not exceed an amount that would adversely affect the antimicrobial activity of the composition. The composition preferably contains hydrogen peroxide at a minimal concentration.

Hydrogen peroxide can typically be present in a use solution in an amount of up to about 2500 ppm, preferably between about 3 ppm and about 1850 ppm, and more preferably between about 6 ppm and about 1250 ppm.

Carboxylic Acid

The peracid antimicrobial composition of the disclosure also includes a carboxylic acid. A carboxylic acid includes any compound of the formula R—(COOH)n in which R can be hydrogen, alkyl, alkenyl, alicyclic group, aryl, heteroaryl, or heterocyclic group, and n is 1, 2, or 3. Preferably R includes hydrogen, alkyl, or alkenyl.

The term "alkyl" includes a straight or branched saturated aliphatic hydrocarbon chain having from 1 to 12 carbon atoms, such as, for example, methyl, ethyl, propyl, isopropyl (1-methylethyl), butyl, tert-butyl (1,1-dimethylethyl), and the like.

The term "alkenyl" includes an unsaturated aliphatic hydrocarbon chain having from 2 to 12 carbon atoms, such as, for example, ethenyl, 1-propenyl, 2-propenyl, 1-butenyl, 2-methyl-1-propenyl, and the like.

The above alkyl or alkenyl can be terminally substituted with a heteroatom, such as, for example, a nitrogen, sulfur, or oxygen atom, forming an aminoalkyl, oxyalkyl, or thioalkyl, for example, aminomethyl, thioethyl, oxypropyl, and the like. Similarly, the above alkyl or alkenyl can be interrupted in the chain by a heteroatom forming an alkylaminoalkyl, alkylthioalkyl, or alkoxyalkyl, for example, methylaminoethyl, ethylthiopropyl, methoxymethyl, and the like.

The term "alicyclic" includes any cyclic hydrocarbyl containing from 3 to 8 carbon atoms. Examples of suitable alicyclic groups include cyclopropanyl, cyclobutanyl, cyclopentanyl, etc.

The term "heterocyclic" includes any cyclic hydrocarbyl containing from 3 to 8 carbon atoms that is interrupted by a heteroatom, such as, for example, a nitrogen, sulfur, or oxygen atom. Examples of suitable heterocyclic groups include groups derived form tetrahydrofurans, furans, thiophenes, pyrrolidines, piperidines, pyridines, pyrrols, picoline, coumaline, etc.

Alkyl, alkenyl, alicyclic groups, and heterocyclic groups can be unsubstituted or substituted by, for example, aryl, heteroaryl, $C_{1-4}$ alkyl, $C_{1-4}$ alkenyl, $C_{1-4}$ alkoxy, amino, carboxy, halo, nitro, cyano, —$SO_3H$, phosphono, or hydroxy. When alkyl, alkenyl, alicyclic group, or heterocyclic group is substituted, preferably the substitution is $C_{1-4}$ alkyl, halo, nitro, amido, hydroxy, carboxy, sulpho, or phosphono. In one embodiment, R includes alkyl substituted with hydroxy.

The term "aryl" includes aromatic hydrocarbyl, including fused aromatic rings, such as, for example, phenyl and naphthyl.

The term "heteroaryl" includes heterocyclic aromatic derivatives having at least one heteroatom such as, for example, nitrogen, oxygen, phosphorus, or sulfur, and includes, for example, furyl, pyrrolyl, thienyl, oxazolyl, pyridyl, imidazolyl, thiazolyl, isoxazolyl, pyrazolyl, isothiazolyl, etc.

The term "heteroaryl" also includes fused rings in which at least one ring is aromatic, such as, for example, indolyl, purinyl, benzofuryl, etc.

Aryl and heteroaryl groups can be unsubstituted or substituted on the ring by, for example, aryl, heteroaryl, alkyl, alkenyl, alkoxy, amino, carboxy, halo, nitro, cyano, —$SO_3H$, phosphono, or hydroxy. When aryl, aralkyl, or heteroaryl is substituted, preferably the substitution is $C_{1-4}$ alkyl, halo, nitro, amido, hydroxy, carboxy, sulpho, or phosphono. In one embodiment, R includes aryl substituted with $C_{1-4}$ alkyl.

Examples of suitable carboxylic acids include a variety monocarboxylic acids, dicarboxylic acids, and tricarboxylic acids.

Monocarboxylic acids include, for example, formic acid, acetic acid, propanoic acid, butanoic acid, pentanoic acid, hexanoic acid, heptanoic acid, octanoic acid, nonanoic acid, decanoic acid, undecanoic acid, dodecanoic acid, glycolic acid, lactic acid, salicylic acid, acetylsalicylic acid, mandelic acid, etc.

Dicarboxylic acids include, for example, adipic acid, fumaric acid, glutaric acid, maleic acid, succinic acid, malic acid, tartaric acid, etc.

Tricarboxylic acids include, for example, citric acid, trimellitic acid, isocitric acid, agaicic acid, etc.

A carboxylic acid suitable for use in the composition can be selected for its solubility, cost, approval as food additive, odor, purity, etc.

A particularly useful carboxylic acid includes a carboxylic acid that is water soluble such as formic acid, acetic acid, propionic acid, butanoic acid, lactic acid, glycolic acid, citric acid, mandelic acid, glutaric acid, maleic acid, malic acid, adipic acid, succinic acid, tartaric acid, etc. These carboxylic acids can also be useful because water-soluble carboxylic acids can be food additives such as formic acid, acetic acid, lactic acid, citric acid, tartaric acid, etc.

Preferably the composition includes acetic acid, octanoic acid, or propionic acid, lactic acid, heptanoic acid, or nonanoic acid.

The composition can include a carboxylic acid in an amount that can be effectively removed from the inside and outside of a package in an aseptic filler during the rinsing step of the aseptic packaging process. A carboxylic acid can typically be present in a use solution in an amount less than 40000 ppm, preferably less than 30000 ppm and more preferably less than 20000 ppm.

Peracid

The composition also includes a peracid. A peracid is also known in the art as a percarboxylic acid, a peroxyacid, and a peroxycarboxylic acid.

A peracid includes any compound of the formula R—(COOOH)$_n$ in which R can be hydrogen, alkyl, alkenyl, alicyclic group, aryl, heteroaryl, or heterocyclic group, and n is 1, 2, or 3. Preferably R includes hydrogen, alkyl, or alkenyl.

The terms "alkyl," "alkenyl," "alicyclic group," "aryl," "heteroaryl," and "heterocyclic group" are as defined above.

Peracids used in the composition include any peroxycarboxylic acid that can be prepared from the acid-catalyzed equilibrium reaction between a carboxylic acid described above and hydrogen peroxide described above. Preferably, the composition includes peroxyacetic acid, peroxyoctanoic acid, or peroxypropionic acid, peroxylactic acid, peroxyheptanoic acid, peroxyoctanoic acid, or peroxynonanoic acid.

A peroxycarboxylic acid can also be prepared by the autoxidation of aldehydes or by the reaction of hydrogen peroxide with an acid chloride, acid hydride, carboxylic acid anhydride, or sodium alcoholate.

In some embodiments, a peroxycarboxylic acid includes at least one water-soluble peroxycarboxylic acid in which R includes alkyl of 1-4 carbon atoms. For example, in one embodiment, a peroxycarboxylic acid includes peroxyacetic acid. In another embodiment, a peroxycarboxylic acid has R that is an alkyl of 1-4 carbon atoms substituted with hydroxy.

Methods of preparing peroxyacetic acid are known to those of skill in the art including those disclosed in U.S. Pat. No. 2,833,813, which is incorporated herein by reference.

One advantage of using a peroxycarboxylic acid in which R includes alkyl of 1-4 carbon atoms is that such peroxycarboxylic acids traditionally have a lower pKa than peroxycarboxylic acids having R that is alkyl with more than 4 carbon atoms. This lower pKa can favor a faster rate of peroxycarboxylic acid equilibrium and can be effective for providing a composition of the disclosure with, for example, acidic pH, which can be advantageous for improved lime-scale and/or soil removal.

In other embodiments, a peroxycarboxylic acid includes at least one peroxycarboxylic acid of limited water solubility in which R includes alkyl of 5-12 carbon atoms and at least one water-soluble peroxycarboxylic acid in which R includes alkyl of 1-4 carbon atoms. For example, in one embodiment, a peroxycarboxylic acid includes peroxyacetic acid and at least one other peroxycarboxylic acid such as those named above. Preferably, the composition includes peroxyacetic acid and peroxyoctanoic acid.

One advantage of combining a water-soluble carboxylic acid or peroxycarboxylic acid with a carboxylic acid or peroxycarboxylic acid having limited water solubility is that the water-soluble carboxylic acid or peroxycarboxylic acid can provide a hydrotropic effect upon less water soluble carboxylic and peroxycarboxylic acids, which can facilitate uniform dispersion and/or consequent physical stability within the composition.

Another advantage of this combination of peroxycarboxylic acids is that it can provide a composition of the disclosure with desirable antimicrobial activity in the presence of high organic soil loads.

The composition can include a peroxycarboxylic acid, or mixtures thereof, in an amount effective for the sterilization of bacterial and fungal spores of public health and spoilage significance on the inside and outside surfaces of a food package in an aseptic filler as well as within the enclosure of the filler itself. A peroxycarboxylic acid can typically be present in this composition in an amount of between about 500 ppm and about 6000 ppm, preferably between about 1000 ppm and 5000 ppm, and more preferably between about 1500 ppm and about 4000 ppm.

Additional Optional Materials

The composition can optionally include additional ingredients to enhance the composition including stabilizing agents, hydrotropes, surfactants, defoamers, corrosion inhibitors, rheology modifiers, dyes, and fragrances.

Stabilizing Agents

The composition can optionally include stabilizing agents to stabilize the peracid and hydrogen peroxide and prevent the premature oxidation of this constituent within the composition.

Chelating agents or sequestrants generally useful as stabilizing agents in the present compositions include phosphonic acid and phosphonates, phosphates, aminocarboxylates and their derivatives, pyrophosphates, ethylenediamine and ethylenetriamine derivatives, hydroxyacids, and mono-, di-, and tri-carboxylates and their corresponding acids. Other chelating agents include nitroloacetates and their derivatives, and mixtures thereof. Examples of aminocarboxylates include amino acetates and salts thereof. Suitable amino acetates include: N-hydroxyethylaminodiacetic acid; hydroxyethylenediaminetetraacetic acid; nitrilotriacetic acid (NTA); ethylenediaminetetraacetic acid (EDTA); N-hydroxyethyl-ethylenediaminetriacetic acid (HEDTA); tetrasodium ethylenediaminetetraacetic acid (EDTA); diethylenetriaminepentaacetic acid (DTPA); Na$_2$EDG, ethanoldiglycine, methylglycinediacetic acid (MGDA), salts of L-glutamic acid N,N-diacetic acid (GLDA), N,N-bis(carboxylatomethyl)-L-glutamate; EDDS, [S—S]-ethylenediaminedisuccinic acid; and 3-hydroxy-2,2'-iminodisuccinate, alanine-N, N-diacetic acid; n-hydroxyethyliminodiacetic acid; and the like; their alkali metal salts; and mixtures thereof. Suitable aminophosphates include nitrilotrismethylene phosphates and other aminophosphates with alkyl or alkaline groups with less than 8 carbon atoms. Exemplary polycarboxylates iminodisuccinic acids (IDS), sodium polyacrylates, citric acid, gluconic acid, oxalic acid, salts thereof, mixtures thereof, and the like. Additional polycarboxylates include citric or citrate-type chelating agents, polymeric polycarboxylate, and acrylic or polyacrylic acid-type chelating agents. Additional chelating agents include polyaspartic acid or co-condensates of aspartic acid with other amino acids, C$_4$-C$_{25}$-mono- or -dicarboxylic acids and C$_4$-C$_{25}$-mono- or -diamines. Exemplary polymeric polycarboxylates include polyacrylic acid, maleic/olefin copolymer, acrylic/maleic copolymer, polymethacrylic acid, acrylic acid-methacrylic acid copolymers, hydrolyzed polyacrylamide, hydrolyzed polymethacrylamide, hydrolyzed polyamide-methacrylamide copolymers, hydrolyzed polyacrylonitrile, hydrolyzed polymethacrylonitrile, hydrolyzed acrylonitrile-methacrylonitrile copolymers, and the like.

The chelating agent can be present in an amount from about 0.01 to about 5 wt. %, from about 0.05 to about 3 wt. %, and from about 0.1 to about 1.5 wt. %.

Hydrotropes

The composition can optionally include a hydrotrope coupler or solubilizer. Such materials can be used to ensure that the composition remains phase stable and in a single highly active aqueous form. Such hydrotrope solubilizers or couplers can be used at concentrations that maintain phase stability but do not result in unwanted compositional interaction.

Representative classes of hydrotrope solubilizers or coupling agents include an anionic surfactant such as an alkyl sulfate, an alkyl or alkane sulfonate, a linear alkyl benzene or naphthalene sulfonate, a secondary alkane sulfonate, alkyl ether sulfate or sulfonate, an alkyl phosphate or phosphonate, dialkyl sulfosuccinic acid ester, sugar esters (e.g., sorbitan esters) and a $C_{8-10}$ alkyl glucoside.

Coupling agents can also include n-octane sulfonate, aromatic sulfonates such as an alkyl aryl sulfonate (e.g., sodium xylene sulfonate or naphthalene sulfonate), and alkylated diphenyl oxide disulfonic acids, such as those sold under the DOWFAX™ trade name, preferably the acid forms of these hydrotropes.

The concentration of hydrotrope useful in the present disclosure generally ranges from about 0.1 to about 20 wt-%, preferably from about 2 to about 18 wt-%, most preferably from about 3 to about 15 wt-%.

Surfactants

The composition can optionally include a surfactant or mixture of surfactants. The surfactant may include anionic, nonionic, cationic, and zwitterionic surfactants, which are commercially available, and mixtures thereof. In an embodiment, the surfactant includes a nonionic or anionic surfactant. For a discussion of surfactants, see Kirk-Othmer, *Encyclopedia of Chemical Technology*, Third Edition, volume 8, pages 900-912.

Nonionic surfactants can include those having a polyalkylene oxide polymer as a portion of the surfactant molecule. These surfactants can be capped or uncapped. Such nonionic surfactants include, for example, chlorine-, benzyl-, methyl-, ethyl-, propyl-, butyl- and other like alkyl-capped polyethylene glycol ethers of fatty alcohols; polyalkylene oxide free nonionics such as alkyl polyglycosides; sorbitan and sucrose esters and their ethoxylates; alkoxylated ethylene diamine; alcohol alkoxylates such as alcohol ethoxylate propoxylates, alcohol propoxylates, alcohol propoxylate ethoxylate propoxylates, alcohol ethoxylate butoxylates, fatty alcohol ethoxylates (e.g., tridecyl alcohol alkoxylate, ethylene oxide adduct), and the like; nonylphenol ethoxylate, polyoxyethylene glycol ethers, and the like; carboxylic acid esters such as glycerol esters, polyoxyethylene esters, ethoxylated and glycol esters of fatty acids, and the like; carboxylic amides such as diethanolamine condensates, monoalkanolamine condensates, polyoxyethylene fatty acid amides, and the like; and polyalkylene oxide block copolymers including an ethylene oxide/propylene oxide block copolymer such as those commercially available under the trademark PLURONIC (BASF-Wyandotte), and the like; ethoxylated amines and ether amines commercially available from Tomah Corporation and other like nonionic compounds. Silicone surfactants such as the ABIL B8852 (Goldschmidt) can also be used.

The nonionic surfactant can include linear and secondary alcohol ethoxylates (fatty alcohol ethoxylates, e.g., tridecyl alcohol alkoxylate, ethylene oxide adduct), alkyl phenol ethoxylates, ethoxy/propoxy block surfactants, and the like. Examples of preferred linear and secondary alcohol ethoxylates (fatty alcohol ethoxylates, e.g., tridecyl alcohol alkoxylate, ethylene oxide adduct) include five mole ethoxylate of linear, primary 12-14 carbon number alcohol ($C_{12-14}H_{25-29}$)—O—($CH_2CH_2O$)$_5$H (one of which is sold under the tradename LAE 24-5), seven mole ethoxylate of linear, primary 12-14 carbon number alcohol ($C_{12-14}H_{25-29}$)—O—($CH_2CH_2O$)$_7$H (one of which is sold under the tradename LAE 24-7), twelve mole ethoxylate of linear, primary 12-14 carbon number alcohol ($C_{12-14}H_{25-29}$)—O—($CH_2CH_2O$)$_{12}$H (one of which is sold under the tradename LAE 24-12), and the like.

Anionic surfactants can include, for example, carboxylates such as alkylcarboxylates (carboxylic acid salts) and polyalkoxycarboxylates, alcohol ethoxylate carboxylates, nonylphenol ethoxylate carboxylates, and the like; sulfonates such as alkylsulfonates, alkylbenzenesulfonates (e.g., linear dodecyl benzene sulfonic acid or salts thereof), alkylarylsulfonates, sulfonated fatty acid esters, and the like; sulfates such as sulfated alcohols, sulfated alcohol ethoxylates, sulfated alkylphenols, alkylsulfates, sulfosuccinates, alkylether sulfates, and the like; and phosphate esters such as alkylphosphate esters, ethoxylated alcohol phosphate esters, and the like. Preferred anionics include sodium alkylarylsulfonate, alkylbenzenesulfonates (e.g., linear dodecyl benzene sulfonic acid or salts thereof), and the like.

Surface active substances are classified as cationic if the charge on the hydrophilic portion of the molecule is positive. Surfactants in which the hydrophile carries no charge unless the pH is lowered close to neutrality or lower, but which are then cationic (e.g. alkyl amines), are also included in this group.

Cationic surfactants can include compounds containing at least one long carbon chain hydrophobic group and at least one positively charged nitrogen. The long carbon chain group may be attached directly to the nitrogen atom by simple substitution; or indirectly by a bridging functional group or groups in so-called interrupted alkylamines and amido amines. Such functional groups can make the molecule more hydrophilic and/or more water dispersible, more easily water solubilized by co-surfactant mixtures, and/or water soluble. For increased water solubility, additional primary, secondary or tertiary amino groups can be introduced or the amino nitrogen can be quaternized with low molecular weight alkyl groups. Further, the nitrogen can be a part of a branched or straight chain moiety of varying degrees of unsaturation or of a saturated or unsaturated heterocyclic ring. In addition, cationic surfactants may contain complex linkages having more than one cationic nitrogen atom.

The cationic surfactant can include a quaternary ammonium surfactant, such as tallow quaternary ammonium surfactant, such as a tallow amine ethoxylate quaternary ammonium compound. For example, a tallow amine ethoxylate quaternary ammonium compound can include a quaternary nitrogen bonded to a methyl group, a tallow moiety, and two ethoxylate moieties. The ethoxylate moieties can include 6-10 ethoxylate groups. In an embodiment, the present composition can include about 1 to about 10 wt-% or about 5 wt-% of such a cationic surfactant.

The surfactant compounds classified as amine oxides, amphoterics and zwitterions are themselves typically cationic in near neutral to acidic pH solutions and can overlap surfactant classifications. Polyoxyethylated cationic surfactants generally behave like nonionic surfactants in alkaline solution and like cationic surfactants in acidic solution.

The majority of large volume commercial cationic surfactants can be subdivided into four major classes and additional sub-groups, for example, as described in "Surfactant Encyclopedia", *Cosmetics & Toiletries*, Vol. 104 (2) 86-96 (1989). The first class includes alkylamines and their salts. The second class includes alkyl imidazolines. The third class includes ethoxylated amines. The fourth class includes quaternaries, such as alkylbenzyldimethylammonium salts, alkyl benzene salts, heterocyclic ammonium salts, dialkylammonium salts, and the like. Cationic surfactants are known to have a variety of properties that can be beneficial in the present compositions. These desirable properties can include detergency, antimicrobial efficacy, and the like.

Defoamers

The composition can optionally include defoamers. Generally, defoamers can include silica and silicones; aliphatic acids or esters; alcohols; sulfates or sulfonates; amines or amides; halogenated compounds such as fluorochlorohydrocarbons; vegetable oils, waxes, mineral oils as well as their sulfated derivatives; and phosphates and phosphate esters such as alkyl and alkaline diphosphates, and tributyl phosphates among others; and mixtures thereof.

Food grade defoamers are preferred. To this end, one of the more effective antifoaming agents includes silicones. Silicones such as dimethyl silicone, glycol polysiloxane, methylphenol polysiloxane, trialkyl or tetralkyl silanes, hydrophobic silica defoamers and mixtures thereof can all be used in defoaming applications. Commercial defoamers commonly available include silicones such as Ardefoam® from Armour Industrial Chemical Company which is a silicone bound in an organic emulsion; Foam Kill® or Kresseo® available from Krusable Chemical Company which are silicone and non-silicone type defoamers as well as silicone esters; and Anti-Foam A® and DC-200 from Dow Corning Corporation which are both food grade type silicones among others. These defoamers can be present at a concentration range from about 0.01 wt-% to 5 wt-%, preferably from about 0.01 wt-% to 2 wt-%, and most preferably from about 0.01 wt-% to about 1 wt-%.

Corrosion Inhibitors

The composition can optionally include a corrosion inhibitor. Useful corrosion inhibitors include polycarboxylic acids such as short chain carboxylic diacids, triacids, as well as phosphate esters and combinations thereof. Useful phosphate esters include alkyl phosphate esters, monoalkyl aryl phosphate esters, dialkyl aryl phosphate esters, trialkyl aryl phosphate esters, and mixtures thereof such as Emphos PS 236 commercially available from Witco Chemical Company. Other useful corrosion inhibitors include the triazoles, such as benzotriazole, tolyltriazole and mercaptobenzothiazole, and in combinations with phosphonates such as 1-hydroxyethylidene-1,1-diphosphonic acid, and surfactants such as oleic acid diethanolamide and sodium cocoamphohydroxy propyl sulfonate, and the like. Useful corrosion inhibitors include polycarboxylic acids such as dicarboxylic acids. The acids which are preferred include adipic, glutaric, succinic, and mixtures thereof. The most preferred is a mixture of adipic, glutaric and succinic acid, which is a raw material sold by BASF under the name SOKALAN® DCS.

Rheology Modifiers

The composition can optionally include one or more rheology modifiers. Water soluble or water dispersible rheology modifiers that are useful can be classified as inorganic or organic. The organic thickeners can further be divided into natural and synthetic polymers with the latter still further subdivided into synthetic natural-based and synthetic petroleum-based.

Inorganic thickeners are generally compounds such as colloidal magnesium aluminum silicate (VEEGUM®), colloidal clays (Bentonites), or silicas (CAB-O-SILS®) which have been fumed or precipitated to create particles with large surface to size ratios. Suitable natural hydrogel thickeners are primarily vegetable derived exudates. For example, tragacanth, karaya, and acacia gums; and extractives such as carrageenan, locust bean gum, guar gum and pectin; or, pure culture fermentation products such as xanthan gum. Chemically, all of these materials are salts of complex anionic polysaccharides. Synthetic natural-based thickeners having application are cellulose derivatives wherein the free hydroxyl groups on the linear anhydro-glucose polymers have been etherified or esterified to give a family of substances, which dissolve in water and give viscous solutions. This group of materials includes the alkyl and hydroxyllalkycelluloses, specifically methylcellulose, hydroxyethylmethylcellulose, hydroxypropylmethylcellulose, hydroxybutylmethycellulose, hydroxyethylcellulose, ethylhydroxyethylcellulose, hydroxypropylcellulose, and carboxymethylcellulose. Synthetic petroleum-based water soluble polymers are prepared by direct polymerization of suitable monomers of which polyvinylpyrrolidone, polyvinylmethylether, polyacrylic acid and polymethacrylic acid, polyacrylamide, polyethylene oxide, and polyethyleneimine are representative.

Dyes and Fragrances

The composition can optionally include various dyes, odorants including perfumes, and other aesthetic enhancing agents. Preferred dyes include FD&C dyes, D&C dyes, and the like.

Examples of containers that can be filled include polyethylene terephthalate (PET), high density polyethylene (HDPE), polypropylene (PP), low density polyethylene, polycarbonate (PC), poly vinyl alcohol (PVA), aluminum, single or multilayer films or pouches, paperboard, steel, glass, multilayer bottles, other polymeric packaging material, combinations of these materials in films, pouches, bottle, or other food packaging materials.

Figure 4:
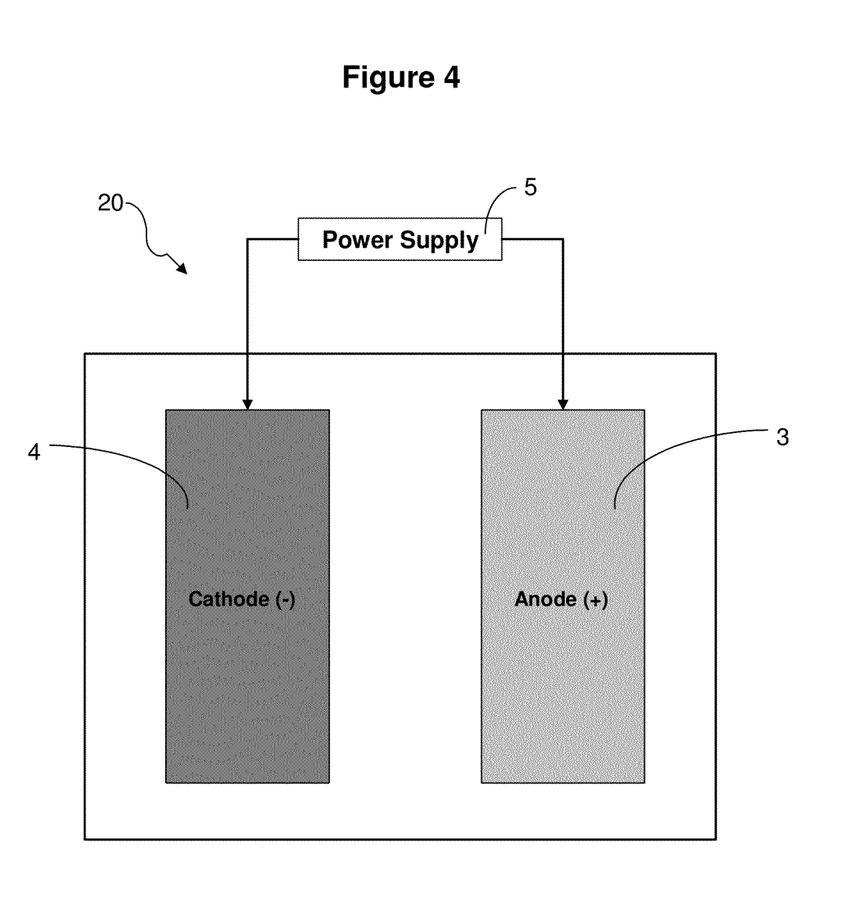
FIG. 4 shows a schematic of an exemplary single cell.

The present disclosure also uses a single cell to degrade desired components in a solution. FIG. 4 illustrates an exemplary single cell. The single cell 20 includes an anode 3 and a cathode 4 in the same cell. The anode 3 and cathode 4 are both connected to a power supply 5. This single cell 20 can be used in an industrial application to degrade certain components in a solution. For example, in aseptic packaging operations, the single cell 20 can be provided in fluid communication with a rinse, in order to degrade certain components of the rinse. In some cases, an antimicrobial composition comprising hydrogen peroxide, carboxylic acid, and peracid is used to sterilize food packages and a rinse accumulates hydrogen peroxide and peracid during rinsing. Here, the single cell 20 can be used to degrade predetermined amounts of the hydrogen peroxide and peracid in the rinse.

Figure 5:
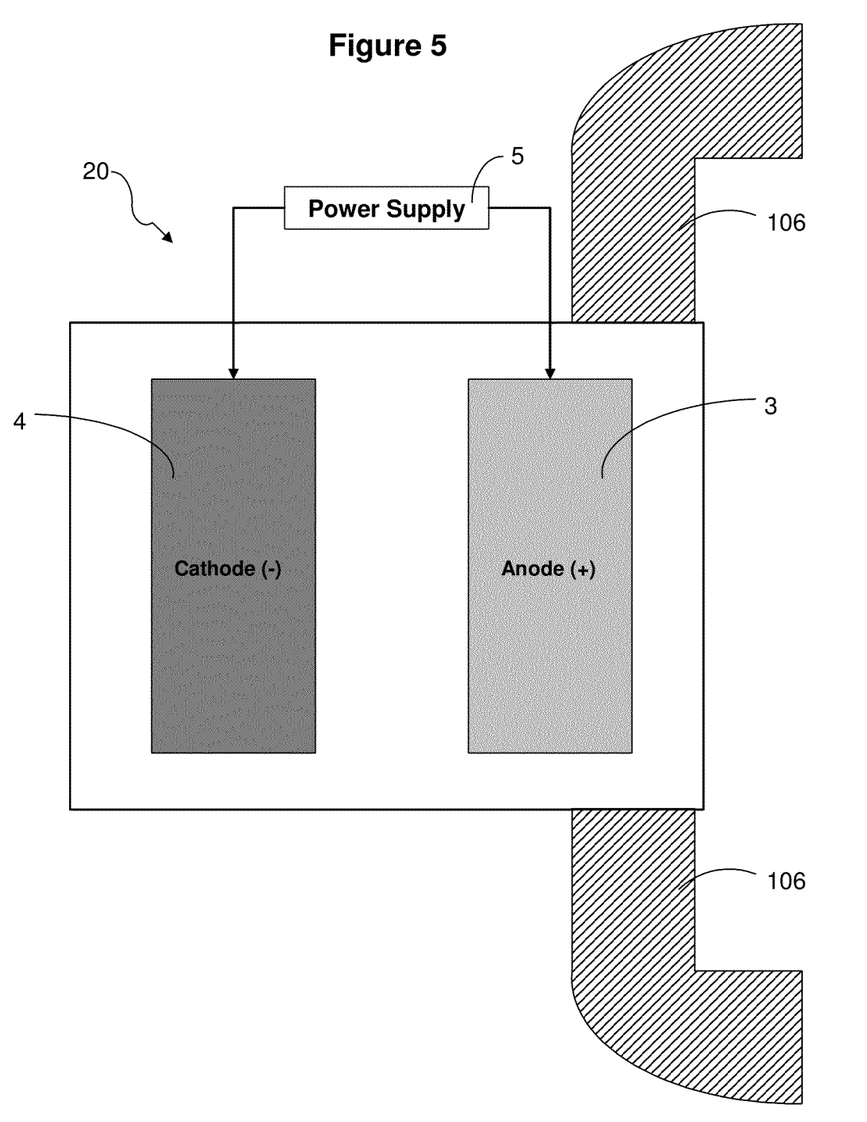
FIG. 5 shows a schematic of one embodiment of integrating a single cell into an aseptic packaging operation.

FIG. 5 illustrates a single cell 20 that is integrated with the plant 100 of FIG. 2. In FIG. 5, the single cell 20 is integrated with the drain 106 of the plant 100. However, skilled artisans will understand that the cell 20 can instead be integrated with other parts of the plant 100. Likewise, the plant 100 can be of any desired design and need not include only one single cell 20.

In the integrated single cell of FIG. 5, the cell is in fluid communication with the drain 106. Rinse solution in the drain 106 moves through the cell 20. As this happens, certain desired components are degraded from the rinse and continue thereon through the drain 106, where it is either recycled back to the plant 100 or removed from the plant 100.

For a more complete understanding of the disclosure, the following examples are given to illustrate some embodiments. These examples and experiments are to be understood as illustrative and not limiting.

EXAMPLES

Example 1

Single Cell Experiment

Example 1 examined the ability of a single chamber electrical cell to selectively decompose hydrogen peroxide in the presence of peroxyacetic acid ("POAA"). For this example, two 1"×3"×0.25" electrically conductive graphite electrodes were suspended in a single beaker containing a solution of POAA made up from a sample of a 15% POAA equilibrium concentrate. The beaker was placed on a stirplate and the electrodes were connected by wire to a variable output power supply. The test fixture was held at room temperature for the duration of the test.

A voltage of 12 VDC at a current of 0.08 A was applied to the solution and the concentration of hydrogen peroxide and POAA was measured by titration at zero, one and six hours. The concentration of each was measured via titration of a 10 ml aliquot of the test solution diluted in ~100 ml of ice water. POAA concentration is measured by iodometric titration which entails addition of 1-2 ml of 10.0% KI solution along with 2-3 drops of starch indicator followed by titration with 0.1N sodium thiosulfate to a colorless endpoint. Peroxide content is measured by addition of 1-2 ml concentrated sulfuric acid and 4-5 drops of an oxygen catalyst (saturated solution of ammonium molybdate) to the same solution followed by titration with 0.1N sodium thiosulfate to the final colorless endpoint.

POAA concentration is calculated via the following calculation:

$$ppm\ POAA = \frac{(ml\ Na_2S_2O_3)(Normality\ of\ titrant)(Equivalent\ wt\ POAA)}{(sample\ size)(2)}$$

$$ppm\ POAA = \frac{(ml\ Na_2S_2O_3)(0.1)(76)}{(10\ g)(2)}$$

Peroxide concentration is calculated via the following calculation:

$$ppm\ H_2O_2 = \frac{(ml\ Na_2S_2O_3)(Normality\ of\ titrant)(Equivalent\ wt\ H_2O_2)}{(sample\ size)(2)}$$

$$ppm\ POAA\ or\ H_2O_2 = \frac{(ml\ Na_2S_2O_3)(0.1)(34)}{(10\ g)(2)}$$

The concentrations of hydrogen peroxide and POAA are shown in Table 1.

TABLE 1

POAA Concentration (ppm) and Hydrogen Peroxide Concentration (ppm) Over Time (hours).

| Time (Hours) | POAA titration | $H_2O_2$ titration |
|---|---|---|
| 0 | 5.05 ml/1919 ppm | 14.75 ml/1649 ppm |
| 1 | 5.05 ml/1919 ppm | 14.6 ml/1623 ppm |
| 6 | 4.0 ml/1520 ppm | 12.45 ml/1436 ppm |

Table 1 shows that there is little selectivity in degradation of POAA and hydrogen peroxide in this experiment. This is likely due to the fact that both an oxidizing and reducing potential is present in the solution since both anode and cathode are in the same beaker. Thus, Table 1 shows that the single cell did not selectively degrade hydrogen peroxide. However, a single cell is indeed beneficial in degrading both hydrogen peroxide and POAA.

Example 2

Split Cell Experiment

Example 2 compared the ability of a split electrical cell to decompose hydrogen peroxide selectively in the presence of POAA. This experiment was similar to the experiment in Example 1 with the exception that the anode and cathode were separated into two separate beakers.

One liter of a POAA/hydrogen peroxide solution was split evenly between the two beakers. The two beakers were then connected by a salt bridge. The salt bridge was made by making a 1.0N solution of sodium nitrate and solidifying that solution with 1.0% agar. This mixture was poured into a ½ inch plastic tube while still hot where it solidified. One end of this tube was placed in the beaker containing the anode while the other end was placed in the beaker containing the cathode forming a salt bridge between the 2 beakers/cells.

The power source was again the 1"×3"×0.25" electrically conductive graphite electrodes connected to a variable power supply. A voltage of 22 VDC at a current of 0.04 A was applied to the solution and the level of POAA and hydrogen peroxide were measured by titration at the anode (positive connection) and at the cathode (negative connection) at several time points to determine the impact of the electrical potential on the stability of both POAA and hydrogen peroxide. The concentration of the POAA and the hydrogen peroxide was measured at time zero and at five hours in the same manner as outlined in Example 1. The concentrations of both POAA and hydrogen peroxide are shown in Table 2. Also, control samples are shown, which are samples of a POAA solution to which no electrical potential was applied.

TABLE 2

POAA Concentration and Hydrogen Peroxide Concentration (ppm) Over Time (hours).

| Time (Hours) | POAA/ Cathode | H$_2$O$_2$/ Cathode | POAA/ Anode | H$_2$O$_2$/ Anode | POAA/ Control | H$_2$O$_2$/ Control |
|---|---|---|---|---|---|---|
| 0 | 7.85 ml | 22.8 ml | 7.85 ml | 22.8 ml | 7.85 | 22.8 ml |
|   | 2983 ppm | 2541 ppm | 2983 ppm | 2541 ppm | 2983 ppm | 2541 ppm |
| 5 | 3.90 ml | 18.2 ml | 7.55 ml | 19.4 ml | 7.7 ml | 23.3 ml |
|   | 1482 ppm | 2431 ppm | 2869 ppm | 2014 ppm | 2926 ppm | 2652 ppm |
| % change | −50% | −4.3% | −3.8% | −20.7% | −1.6% | +4.36% |

Comparison of the peracid and peroxide concentrations in the anode versus the cathode cells shown in Table 2 shows that the split cell was able to selectively degrade hydrogen peroxide in the presence of POAA at the anode with virtually no impact on the stability of the POAA concentration. Table 2 also shows the necessity of separating the anode reaction from the cathode reaction to achieve the intended technical effect and selectively degrade peroxide. Table 1 shows that when the anode and cathode are placed in the same cell, they degrade smaller amounts of both hydrogen peroxide and peracid. But, when the anode and cathode are split with a salt bridge between the two cells, the cathode side selectively degrades the peracid compared to the peroxide, and the anode side selectively degrades the peroxide compared to the peracid. Thus, a split cell is required for selective electrochemical degradation of peroxide in the presence of peracid. And, the anode portion of the split cell should preferably be in direct fluid communication with the peracid/peroxide solution so that it can selectively degrade the peroxide, whereas the cathode portion of the cell will be in electrical communication with the peracid solution through the salt bridge, but is otherwise kept separate from the peracid solution so that it will not reduce the solution.

The foregoing summary, detailed description, and examples provide a sound basis for understanding the disclosure, and some specific example embodiments of the disclosure. Since the invention can comprise a variety of embodiments, the above information is not intended to be limiting. The invention resides in the claims.

We claim:

1. A method of treating a rinse solution comprising:
   (a) applying a rinse solution to a surface of a food package and forming a used rinse solution;
   (b) collecting the used rinse solution, the used rinse solution containing the hydrogen peroxide and peracid;
   (c) transporting the used rinse solution using a rinse line;
   (d) integrating a single electrolytic cell into the rinse line; and
   (e) using the single electrolytic cell to degrade predetermined amounts of the hydrogen peroxide and peracid in the used rinse.

2. The method of claim 1, wherein the rinse solution is a rinse from aseptic packaging applications.

3. The method of claim 1, wherein the peracid is selected from the group consisting of peracetic acid, peroctanoic acid, and mixtures thereof.

4. The method of claim 1, wherein the single electrolytic cell comprises an anode and a cathode.

5. The method of claim 1, wherein the predetermined amounts of hydrogen peroxide and peracid are:
   (a) from about 0.00001 to about 0.5 wt. % hydrogen peroxide; and
   (b) from about 0.1 to about 2.0 wt. % of peracid.

6. The method of claim 1, wherein the single electrolytic cell further comprises a power supply.

* * * * *